United States Patent [19]

Schumacher

[11] Patent Number: 5,289,716
[45] Date of Patent: Mar. 1, 1994

[54] MONITORING AND ANALYZING WASTE GLASS COMPOSITIONS

[75] Inventor: Ray F. Schumacher, Aiken, S.C.

[73] Assignee: The United States of America as represented by the United States Department of Energy, Washington, D.C.

[21] Appl. No.: 933,153

[22] Filed: Aug. 21, 1992

[51] Int. Cl.$^5$ .............................................. G01N 11/00
[52] U.S. Cl. ............................... 73/54.19; 73/54.15
[58] Field of Search ............... 73/54.01, 54.04, 54.07, 73/54.15, 54.19, 439; 324/439, 441, 446; 340/604, 606, 620

[56] References Cited

U.S. PATENT DOCUMENTS

| | | | |
|---|---|---|---|
| 1,780,952 | 11/1930 | Symmes | 73/54.19 |
| 2,604,778 | 7/1952 | Marquardt | 73/302 |
| 2,933,094 | 4/1960 | Cunniff et al. | 137/4 |
| 3,074,277 | 1/1963 | Hill | 73/439 |
| 3,427,198 | 2/1969 | Hill | 134/10 |
| 3,453,891 | 7/1969 | Kapff et al. | 73/439 |
| 3,772,910 | 11/1973 | McGinn et al. | 73/54.19 |
| 3,898,637 | 8/1975 | Wolstenholme | 340/606 |
| 4,359,211 | 11/1982 | Baumert | 266/99 |
| 4,422,326 | 12/1983 | Sasaki | 173/291 |
| 4,526,035 | 7/1985 | Auchapt et al. | 73/439 |
| 4,669,309 | 6/1987 | Cornelius | 73/299 |
| 4,871,000 | 10/1989 | Rittner | 141/95 |
| 4,949,572 | 8/1990 | Wilen et al. | 73/53.01 |
| 5,167,144 | 12/1992 | Schneier | 73/439 |

FOREIGN PATENT DOCUMENTS

| | | | |
|---|---|---|---|
| 2912628 | 10/1980 | Fed. Rep. of Germany | 73/54.15 |
| 0594432 | 2/1978 | U.S.S.R. | 73/54.01 |
| 1603240 | 10/1990 | U.S.S.R. | 73/54.01 |

OTHER PUBLICATIONS

Gardner Laboratory, Inc., "Instruments for Consistency Measurements Viscosity Plasticity Mobility", 1964.

Primary Examiner—Robert J. Warden
Assistant Examiner—Theresa A. Trembley
Attorney, Agent, or Firm—Brian R. Tumm; Harold M. Dixon; William R. Moser

[57] ABSTRACT

A device and method for determining the viscosity of a fluid, preferably molten glass. The apparatus and method uses the velocity of rising bubbles, preferably helium bubbles, within the molten glass to determine the viscosity of the molten glass. The bubbles are released from a tube positioned below the surface of the molten glass so that the bubbles pass successively between two sets of electrodes, one above the other, that are continuously monitoring the conductivity of the molten glass. The measured conductivity will change as a bubble passes between the electrodes enabling an accurate determination of when a bubble has passed between the electrodes. The velocity of rising bubbles can be determined from the time interval between a change in conductivity of the first electrode pair and the second, upper electrode pair. The velocity of the rise of the bubbles in the glass melt is used in conjunction with other physical characteristics, obtained by known methods, to determine the viscosity of the glass melt fluid and, hence, glass quality.

17 Claims, 1 Drawing Sheet

MONITORING AND ANALYZING WASTE GLASS COMPOSITIONS

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention:

The present invention relates to devices and methods for determining physical properties of a conductive fluid. More particularly, the present invention relates to determining the viscosity and specific gravity of molten glass, particularly glass used for encapsulating wastes.

2. Discussion of Background:

Devices and methods for measuring physical properties of electrically conductive fluids such as molten glass are well known. The prior art includes measurement techniques for determining density, specific gravity, and conductivity (or resistivity) of various kinds of fluids, including the constituents added to make glass in a melter.

In U.S. Pat. No. 4,871,000, Ritter describes a method for continually measuring the depth of radioactive glass melt flowing into a mold. The method is based on the electrical resistivity of the glass melt.

Another U.S. Pat. No. 4,422,326 issued to Sasaki, describes a method for measuring density and depth of a glass melt that includes radioactive constituents. Sasaki uses a bubble-type level measuring method to find the minimum pressures required for releasing bubbles into the fluid for density and depth measurements.

Similarly, Baumert, in U.S. Pat. No. 4,359,211, describes the use of bubbles in metallurgical melts for determining the level of a slag layer in a melt. He mentions, but does not describe, determination of melt viscosity and consistency.

In U.S. Pat. No. 2,933,094, Cunniff, et al uses a Wheatstone bridge to determine concentrations of the contents, specific gravity and conductivity of a pickling solution.

Despite the numerous methods and devices existing in the prior art for determining various physical parameters of fluids such as molten glass, since glass quality, especially glass encapsulating waste, is determined by its physical characteristics, there is a need for an accurate method and device for determining the viscosity.

SUMMARY OF THE INVENTION

According to its major aspects and broadly stated, the present invention is a device and method for determining the viscosity of an electrically conductive fluid such as molten glass. In particular, it is an apparatus and method that uses the velocity of rising bubbles of a less dense fluid, preferably helium, within the molten glass to determine the viscosity of the molten glass. The bubbles are generated and released below the surface of the molten glass. The rising bubbles pass between two sets of electrode pairs, one set positioned a known distance above the other, which electrodes are continuously monitoring the conductivity of the molten glass. Since the conductivity between each electrode pair changes as a bubble passes between the electrodes and displaces a portion of the melt, the passing of a bubble between each set of electrodes can be accurately determined. Thus, the velocity of bubbles rising through the glass melt can be determined from the rise time and size of the bubbles. The velocity of the rise of the bubbles in the glass melt is used in conjunction with other physical characteristics, namely density or specific gravity, obtained by known methods, to determine the viscosity of the glass melt fluid.

An important feature of the present invention is the curved portion of the tube for bubble releasing. The plane of the opening of the tube, whence the bubbles are released is vertical. This orientation releases the bubbles more cleanly, consistently and efficiently, thus contributing to the accuracy of computing the bubble rise velocity. Also, the orientation of the face of the curved tube prevents the accumulation of molten glass in the tube that can contribute to the release of malformed bubbles.

Another important feature is use of electrodes to measure the instantaneous location of a bubble in the glass melt. The electrodes measure conductivity continuously and the passing of a bubble between two electrodes has a distinct effect on the conductivity, indicating that a bubble passed between the electrodes at that instant.

Still another important feature of the present invention is the cooperation between the two pairs of electrodes and the bubble releasing tube. The tube opening and both pair of electrodes are spaced apart and aligned so that the bubbles rise from the tube opening and pass between the electrode pairs in sequence. The bubbles reach terminal velocity quickly in the melt and pass at a uniform velocity between the electrode pairs to provide accurate velocity information as input to the viscosity calculation. This feature enables continual, realtime, and remote monitoring of the viscosity of the molten glass.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1:
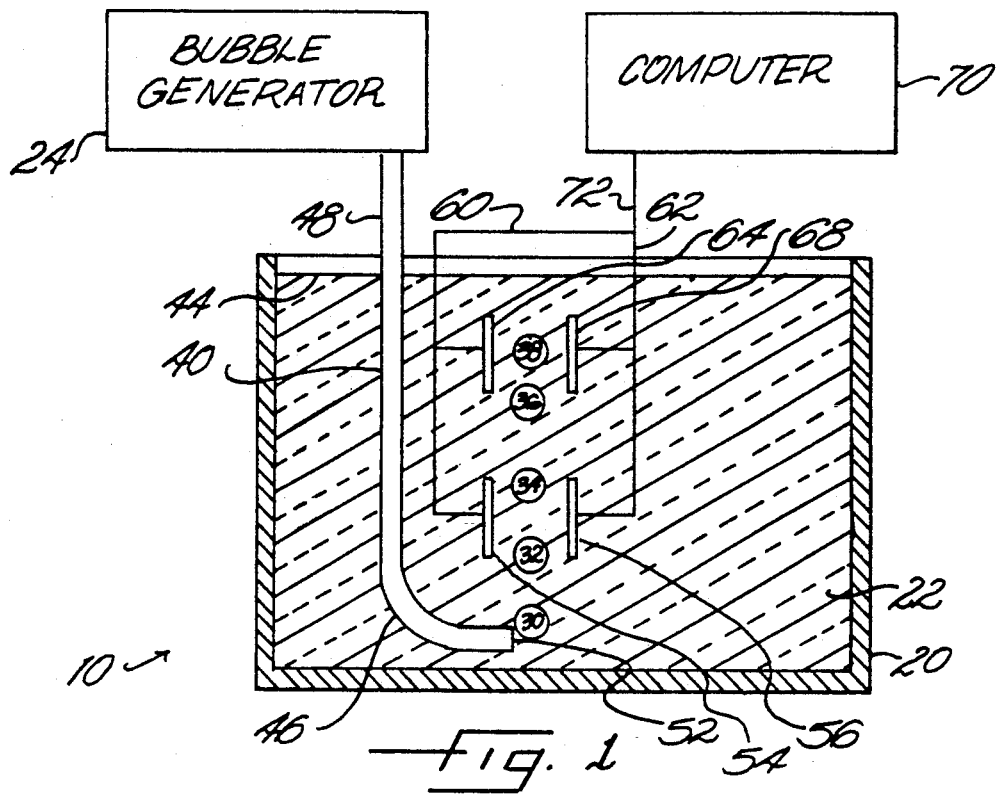
FIG. 1 is a partial cross-sectional view of the apparatus according to a preferred embodiment of the present invention.

Referring now to FIG. 1, an apparatus 10 for determining viscosity comprises a container 20, preferably a glass melter furnace or other molten glass container, carrying a first fluid 22. First fluid 22 is preferably electrically conducting such as molten glass, perhaps with other constituents such as wastes incorporated therein.

A bubble generator 24, preferably located outside of container 20, generates at least one bubble (see generally 30, 32, 34, 36, and 38) of a second fluid in first fluid 22. The second fluid is preferably a gas, especially an inert gas less dense than the first fluid 22, such as helium. A bubble releasing means, such as tube 40, connects to and receives a supply of second fluid from bubble generator 24. Tube 40 releases bubbles of second fluid below the surface (shown generally as 44) of first fluid 22.

Tube 40 further comprises a curved portion 46, preferably bent at an angle of 90° with respect to the vertical portion 48 of tube 40. Furthermore, curved portion 46 has an opening 52 oriented to release bubbles horizontally before they begin rising through first fluid 22.

A first pair of electrodes 54, 56 is preferably spaced apart and vertically aligned with opening 52 of curved portion 46. Additionally, electrodes 54 and 56 are spaced apart from each other to provide space between them, which is ordinarily completely occupied by first fluid 22. A voltage source (not shown) connected by wires, generally indicated as 60 and 62, applies a voltage across electrodes 54 and 56 so that the conductivity of first fluid 22 in the space between electrodes 54 and 56 can be measured.

A second pair of electrodes 64, 68 is preferably spaced apart and located above first electrode pair 54, 56 and opening 52 of curved tube 46. Electrodes 64 and 68 are also spaced apart from each other, which space is also normally completely occupied by first fluid 22. As with first electrode pair 54, 56, a voltage source (not shown), connected by wires 60 and 62, applies a voltage across electrodes 64 and 68 so that the conductivity of first fluid can be measured in the space between electrodes 64 and 68.

Figure 2:
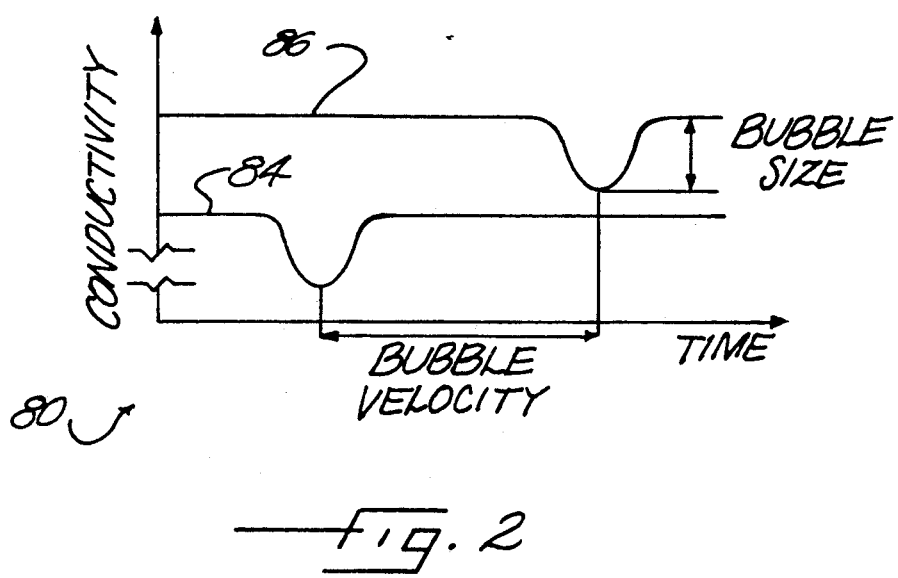
FIG. 2 is a graphical illustration of the operational output of the apparatus according to a preferred embodiment of the present invention.

A computer 70, or other calculating means, is in electrical connection with electrode pairs 54, 56 and 64, 68 to receive in sequence the changes in conductivity that occur as a result of bubbles passing first between electrode pair 54, 56, and then between electrode pair 64, 68 (see generally FIG. 2). Preferably, computer 70 remains in continuous operational communication with first and second electrode pairs via digital output channels, indicated generally by wire group 72. Digital output channels allow conductivity measurement determinations from the outputs of electrode pairs 54, 56 and 64, 68 to be instantaneously acquired by computer 70.

In FIG. 2, an output 80 of device 10 is shown. Generally, output 80 graphically displays the conductivity of first fluid 22 versus time. The conductivity over time of first fluid 22 between electrode pair 54, 56 is shown generally by a first conductivity reading 84. A second conductivity reading 86 generally shows the conductivity over time of first fluid 22 between electrode pair 64, 68.

Viscosity is a difficult physical characteristic to define mathematically with accuracy. However, viscosity for liquids can be determined from Stoke's law:

$$\eta = [2gr^2(\alpha - \rho)]/9v,$$

where $\eta$ is viscosity; g, the acceleration due to gravity; r, the radius of a bubble; $v$, the velocity of a falling sphere (bubble); $\alpha$ the density of the bubble; and $\rho$ the density of first fluid 22. According to the formula, viscosity, $\eta$, will have a negative value since it represents a rising velocity (compared with $v$, the velocity of a falling sphere or bubble). The density of first fluid 22 is also derived from the velocity of the bubble since the velocity is related to the buoyant force on the bubble, which is in turn related in known ways to the relative densities of the first and second fluids.

Viscosity is strongly temperature dependent; a rise of 30° C. will halve the viscosity of molten glass. Glass viscosity can rise by ten orders of magnitude from melting temperature to annealing temperature. Therefore, the temperature of the melt must be known for the viscosity to be meaningful.

Conductivity is the reciprocal of resistivity and is also measured in well-known ways from the current flowing across first fluid 22 from electrode to electrode when a known voltage is applied.

In use, bubble generator 24 generates bubbles of a second fluid that is less dense than first fluid 22, preferably a gas, and most preferably an inert gas such as helium. Tube 40 receives the second fluid and carries it well below surface 44 of first fluid 22. The second fluid then travels through curved portion 46 of tube 40 and is released at opening 52 where it forms a bubble. Although bubbles such as that indicated at 30 are released from curved portion 46 horizontally, they quickly turn vertically to rise toward surface 44 of first fluid 22.

As bubble 30 rises toward surface 44 of first fluid 22, it will pass through the space between first electrode pair 54, 56, as bubble 32 is shown doing. As bubble 32 rises between electrodes 54 and 56, the conductivity being continuously measured between electrode 54 and 56 begins to change, as shown graphically by a decrease of first conductivity reading 84 in FIG. 2. As bubble 32 begins to move beyond the space in first fluid 22 between electrodes 54 and 56, as bubble 34 is shown doing, the conductivity being measured across electrodes 54 and 56 returns to its original or normal value, as shown by a gradual increase of first conductivity reading 84 in FIG. 2.

The bubble continues to rise vertically toward second electrode pair 64, 68. As the bubble begins to occupy the spacing between electrode 64 and 68, as bubble 36 is shown doing, the conductivity being measured between electrodes 64 and 68 begins to change (FIG. 2). The conductivity between electrodes 64 and 68 reaches its maximum change when the bubble is centered between electrode 64 and 68 (see bubble 38), that is, when bubble 38 is displacing the maximum amount of first fluid 22. The conductivity being measured between electrodes 64 and 68 begins to return to its original or normal value as bubble 38 leaves the space between electrodes 64 and 68 (see bubble 34 in FIG. 1; and also second conductivity reading 86 in FIG. 2) and continues rising toward surface 44 of first fluid 22.

Computer 70 continuously monitors the conductivity between electrodes 54, 56 and between electrodes 64, 68 and the time at which there are changes in those conductivities. FIG. 2 shows a graphical output of monitoring the conductivity between electrodes 54, 56, shown by first reading 84, and between electrodes 64, 68, as shown by second reading 86. Since a change in conductivity value across a pair of electrodes represents a bubble passing between them, computer 70 can determine the time interval required for a bubble to rise from one electrode pair to the other. Since first electrode pair 54, 56 and second electrode pair 64, 68 are positioned a fixed and known distance apart, computer 70 can accurately calculate the velocity of the rising bubbles. This bubble rise velocity can then be used with other routine measurements of first fluid 22 to compute various physical properties, including viscosity, of first fluid 22 in accordance with known fluid formulas.

It will be apparent to those skilled in the art that many changes and substitutions can be made to the preferred embodiment herein described without departing from the spirit and scope of the present invention as defined by the appended claims.

What is claimed is:

1. Apparatus for determining the viscosity of a first fluid, said first fluid having a temperature, said apparatus comprising: a container having a first fluid therein;

means for releasing bubbles of a second fluid into said first fluid;

first means for measuring electrical conductivity of said first fluid between a first two points of said first fluid, said first two points located above said releasing means so that when said releasing means releases a bubble, said bubble travels between said first two points thereby causing a first change in electrical conductivity of said first fluid, said first measuring means producing a first output responsive to said first change; and second means for measuring electrical conductivity of said first fluid between a second two points of said first fluid, said second two points located above said releasing means so that when said releasing means releases a bubble, said bubble travels between said second two points thereby causing a second change in electrical conductivity, said second measuring means producing a second output responsive to said second change, said second measuring means spaced apart from said first measuring means by a distance so that the time between the occurrence of said first change and the occurrence of said second change can be used to calculate viscosity of said first fluid.

2. The apparatus as recited in claim 1, wherein said first and second measuring means each further comprises a pair of electrodes and across each of said pair of electrodes a voltage is applied so that said electrical conductivity can be measured.

3. The apparatus as recited in claim 1, wherein said second fluid has a density less than said first fluid, and wherein said releasing means further comprises a curved tube for receiving a flow of said second fluid.

4. The apparatus as recited in claim 1, wherein said releasing means further comprises a curved tube for receiving a flow of said second fluid, said curved tube oriented whereby none of said first fluid can be collected in said curved tube.

5. The apparatus as recited in claim 1, wherein said first fluid further comprises a mixture substantially comprised of molten glass.

6. The apparatus as recited in claim 1, wherein said second fluid is helium.

7. The apparatus as recited in claim 1, wherein said apparatus further comprises:

means for transmitting said first and second outputs from said first and second measuring means, respectively; and means for calculating said viscosity using said first and second outputs, said calculating means in operational communication with said transmitting means and responsive to said first and second outputs.

8. Apparatus for determining the viscosity of a first fluid, said first fluid having a temperature, said apparatus comprising: a container having a first fluid therein;

means for generating bubbles of a second fluid and releasing said bubbles into said first fluid;

a first pair of electrodes in said first fluid, said first pair of electrodes spaced apart and positioned at a first two points, said first electrode pair measuring electrical conductivity of said first fluid between said first two points, said first two points located above said generating means so that when said generating means generates and releases a bubble, said bubble travels between said first two points thereby causing a first change in electrical conductivity of said first fluid between said first two points, said first measuring means producing a first output responsive to said first change; and a second pair of electrodes in said first fluid, said second pair of electrodes spaced apart and positioned at a second two points, said second electrode pair measuring electrical conductivity of said first fluid between said second two points, said second two points located above said generating means so that when said generating means generates and releases a bubble, said bubble travels between said second two points thereby causing a second change in electrical conductivity of said second fluid between said second two points, said second measuring means producing a second output responsive to said second change, said second pair of electrodes spaced apart from said first pair of electrodes by a distance so that the time between said first change and said second change can be used to calculate viscosity of said first fluid.

9. The apparatus as recited in claim 8, wherein said generating means further comprises a curved tube for receiving a flow of said second fluid, said curved tube oriented whereby none of said first fluid can be collected in said curved tube.

10. The apparatus as recited in claim 8, wherein said second fluid is helium.

11. The apparatus as recited in claim 8, wherein said first fluid comprises a mixture substantially comprised of molten glass.

12. The apparatus as recited in claim 8, wherein said apparatus further comprises:

means for transmitting said first and second outputs from said first and second measuring means, respectively; and means for calculating said viscosity using said first and second outputs, said calculating means in operational communication with said transmitting means and responsive to said first and second outputs.

13. A method for determining the viscosity of a fluid, said fluid having a temperature, said method comprising the steps of: providing a container having a fluid therein;

generating a bubble, said bubble rising through said fluid;

measuring by a first pair of electrodes the conductivity of said fluid lying therebetween, said first electrode pair spaced apart so that said bubble passes between said first pair of electrodes whereby the conductivity of said fluid between said second pair of electrodes changes a first time;

measuring by a second pair of electrodes the conductivity of said fluid lying therebetween, said second electrode pair spaced apart so that said bubble passes between said second pair of electrodes whereby the conductivity of said fluid between said second pair of electrodes changes a second time, said first and second pairs of electrodes being separated by a distance;

measuring a time interval between said first time and said second time so that a velocity of said bubble rising said distance can be calculated; and calculating said viscosity of said fluid from said velocity and said temperature of said fluid.

14. The method as recited in claim 13, wherein said bubble generating step further comprises means for generating helium bubbles.

15. The method as recited in claim 13, wherein said bubble generating step further comprises the step of discharging a bubble from a curved tube in fluid communication with said fluid, said curved tube oriented so that said curved tube does not collect said first fluid.

16. The method as recited in claim 13, wherein said fluid is a mixture substantially comprised of molten glass.

17. The method as recited in claim 13, wherein said method further comprises transmitting said first and second outputs from said first and second measuring means, respectively, and calculating said viscosity using said first and second outputs.

* * * * *